(12) United States Patent
Tien et al.

(10) Patent No.: US 11,490,857 B2
(45) Date of Patent: *Nov. 8, 2022

(54) VIRTUAL REALITY BIOFEEDBACK SYSTEMS AND METHODS

(71) Applicant: TAMADE, INC., Pasadena, CA (US)

(72) Inventors: Celine Tien, Pasadena, CA (US); Julien Soros, New York, NY (US); Narae Kim, Pasadena, CA (US)

(73) Assignee: TAMADE, INC., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/357,028

(22) Filed: Jun. 24, 2021

(65) Prior Publication Data

US 2022/0015692 A1 Jan. 20, 2022

Related U.S. Application Data

(63) Continuation of application No. 16/239,484, filed on Jan. 3, 2019, now Pat. No. 11,051,730.

(60) Provisional application No. 61/613,377, filed on Mar. 20, 2012.

(51) Int. Cl.

| | |
|---|---|
| *A61B 5/00* | (2006.01) |
| *G06F 3/01* | (2006.01) |
| *G16H 20/30* | (2018.01) |
| *G06T 19/00* | (2011.01) |
| *A61B 5/0205* | (2006.01) |
| *A61B 5/1486* | (2006.01) |

(52) U.S. Cl.
CPC ............ *A61B 5/486* (2013.01); *A61B 5/0205* (2013.01); *A61B 5/1486* (2013.01); *A61B 5/744* (2013.01); *G06F 3/011* (2013.01); *G06T 19/003* (2013.01); *G16H 20/30* (2018.01)

(58) Field of Classification Search
CPC ..... G06T 19/006; G06T 19/003; A61B 5/486; G16H 20/30; G06F 3/011
See application file for complete search history.

(56) References Cited

U.S. PATENT DOCUMENTS

| | | | |
|---|---|---|---|
| 10,293,565 | B1 | 5/2019 | Tran et al. |
| 10,417,926 | B2 | 9/2019 | Bachani |
| (Continued) | | | |

FOREIGN PATENT DOCUMENTS

WO WO2014124002 8/2014

*Primary Examiner* — Phi Hoang
(74) *Attorney, Agent, or Firm* — Leason Ellis LLP (57) ABSTRACT

A biofeedback virtual reality (VR) system and methods are provided for improving, optimizing, or minimizing the physiological or psychological effects of a medical condition, such as a physiological or psychological condition of a patient. The biofeedback VR System monitors one or more physiological parameters while presenting an immersive VR environment. The system and method comprise a closed-loop biofeedback system where a user (i.e., patient) observes a VR Experience provided by the VR System. The VR System monitors one or more physiological parameters while guiding the user to an improved (or optimized) physiological state through improvement of one or more of the physiological parameters. In some embodiments, a social experience is included in the VR, where the user engages with one or more other users in the VR Experience.

17 Claims, 2 Drawing Sheets

(56) References Cited

U.S. PATENT DOCUMENTS

| | | |
|---|---|---|
| 2007/0270295 A1* | 11/2007 | Balis ................... A63B 26/00 |
| | | 482/142 |
| 2009/0264796 A1 | 10/2009 | Pope et al. |
| 2015/0174362 A1 | 6/2015 | Panova et al. |
| 2018/0207484 A1 | 7/2018 | Briggs et al. |
| 2018/0261332 A1 | 9/2018 | Baeuerle |
| 2019/0030394 A1* | 1/2019 | Orr |
| 2019/0065970 A1* | 2/2019 | Bonutti ............... G08B 21/043 |
| 2019/0159713 A1* | 5/2019 | Kim ..................... A61B 5/162 |
| 2019/0206134 A1* | 7/2019 | Devam ................ G06T 19/00 |
| 2019/0209856 A1 | 7/2019 | Segal |

* cited by examiner

Figure 1

VIRTUAL REALITY BIOFEEDBACK SYSTEMS AND METHODS

BACKGROUND

Body functions, such as heart rate, skin temperature, and blood pressure are controlled involuntarily by the nervous system. Biofeedback has been used to gain control over involuntary functions, using the idea that by harnessing the power of the mind and voluntary functions, and becoming aware of involuntary functions, conditions associated with the involuntary nervous system, such as insomnia, can be treated and/or improved.

Other voluntary functions, such as walking, sitting, standing, reaching, etc. are voluntarily controlled by the nervous system. Systems and methods are known for optimizing and improving voluntary functions, such as optimizing exercise performance.

A combination of involuntary and voluntary nervous system functions contribute to many medical conditions, particularly chronic conditions, and/or the treatment thereof. Further, many medical conditions involve multiple involuntary and voluntary nervous systems functions.

Accordingly, there is a need for improved systems and methods for treating a patient, where the patient can be guided through a therapeutic treatment which provides real-time feedback to allow the patient to improve control over involuntary and voluntary functions to treat a medical condition.

Another difficulty with rehabilitative medical treatments is patient compliance. Patients can become easily bored, or may have anxiety associated with traditional therapies, and not adhere to prescribed protocols for treatment. Accordingly, there is also a need for improved medical treatments that are engaging and/or stress relieving to the patient for increased patient compliance with the medical treatment.

SUMMARY

According to the present invention, a virtual reality biofeedback system and method is provided. The system and method are useful for treating a patient in need thereof, such as a patient suffering from a medical condition, particularly chronic conditions and/or medical conditions involving multiple involuntary and voluntary nervous system functions. The system comprises a virtual reality computing and display system having a virtual reality software system. The virtual reality computing and display system provide the virtual reality experience to the patient. A computing system with components for implementing and processing the virtual reality software system and a display system in communication with the computing system for displaying the virtual reality experience is also provided. The virtual reality experience is transmitted to the patient via the display system. The system has one or more physiological sensors for positioning on a patient body, each sensor, individually monitors at least one physiological signal from the patient body to produce physiological data which are transmitted to the computing system.

The virtual reality system according to the present invention varies the virtual reality experience of the patient in response to the received physiological data of the patient in a biofeedback loop. In the biofeedback loop, the system receives physiological data from the patient and alters the virtual reality experience. In real-time, the patient is instructed to control one or more conditions in the virtual reality experience while controlling or altering one or more physiological signals. The virtual reality system responds to the altered physiological data of the patient, and further alters the virtual reality experience provided to the patient. The patient responds to the altered virtual reality experience by controlling one or more conditions in the virtual reality experience while controlling or altering one or more physiological signals, as instructed by the virtual reality experience. The altered physiological signals are transmitted to the computing system, in a biofeedback loop until a set time or goal for the virtual reality experience is met.

The virtual reality biofeedback system can run two or more virtual reality experiences and provide them to the patient in the same virtual reality session. The virtual reality system varies the virtual reality experience of the patient in response to the received physiological data of the patient in a biofeedback loop, for each individual virtual reality experience. In one embodiment, the patient is instructed to control one or more conditions in the virtual reality experience while controlling or altering a physiological state which is further monitored and received by the computing system. The controlled or altered physiological state for each of the two or more virtual reality experiences is the same or different.

According to another embodiment, a method of treating a patient using a virtual reality experience is provided. According to the method a virtual reality system (VR system) having a VR computing and display system which provides one or more virtual reality experiences to a patient is provided. Each individual virtual reality experience has one or more conditions that can be controlled or altered by the patient. One or more physiological sensors for positioning on a patient body are also provided. Each sensor, individually is capable of monitoring at least one physiological signal from the patient body to produce physiological data. Once the patient is connected to the VR computing and display system via the physiological sensors, a virtual reality experience is then transmitted to the patient by the VR system. The VR system monitors one or more physiological signals from the patient body and transmits the one or more physiological signals to the computing system. The computing system converts the physiological signals to physiological data and alters the virtual reality experience in response to the physiological data. The virtual reality experience of the patient is varied in response to the received physiological data of the patient in a biofeedback loop until a set time or goal for each individual virtual reality experience is met. In the biofeedback loop, first, the virtual reality experience is altered in response to the physiological data. Next, the altered virtual reality experience is transmitted to the patient. Then, the patient is instructed to control one or more conditions in the virtual reality experience while controlling or altering one or more physiological signals. The virtual reality system is then altered in response to the altered physiological data of the patient, and further alters the virtual reality experience provided to the patient. The patient is then instructed to respond to the altered virtual reality experience by controlling one or more conditions in the virtual reality experience while controlling or altering one or more physiological signals, as instructed by the virtual reality experience. The altered physiological signals are transmitted to the computing system in the biofeedback loop until a set time or goal for the virtual reality experience is met. In some embodiments, the virtual reality experience also has a virtual reality social experience where the patient connects with one or more other users on-line for a shared virtual reality experience.

BRIEF DESCRIPTION OF THE DRAWINGS

These and other features, aspects and advantages of the present invention will become better understood from the following description, appended claims, and accompanying figures where:

DESCRIPTION

The present invention provides a virtual reality (VR) biofeedback system and method. The VR biofeedback system (also referred to herein as a "VR System") monitors one or more physiological parameters while presenting an immersive VR environment. The virtual reality biofeedback (also referred to herein as biometric feedback or biometric) system and method of the present invention analyze and incorporate the biometric data (physiological signals such as pulse, respiration, skin conductance, brain waves, etc.) of patients (also referred to herein as a subject or user) for treatment of a medical condition or optimization of a patient's physiology. The system and method comprise a closed-loop biofeedback system where the VR System monitors one or more physiological parameters while guiding the user to an improved (or optimized) physiological state through improvement of one or more of the physiological parameters.

The virtual reality biofeedback systems and methods of the invention provide real-time feedback on a patient's physiological state which allows the patient to improve involuntary and voluntary functions. The systems and methods, as described herein, are designed to engage the user in an immersive VR Experience, which engages the patient and improves patient compliance with a medical treatment. In some embodiments, a social element is incorporated into the system to further engage the patient for increased long-term compliance with the treatment and/or improved performance in the treatment, as the user seeks to improve upon the performance of other users in the social environment provided in the VR Experience.

The VR System comprises physiological sensors that capture real-time physiological signals from the patient. The VR System incorporates the sensor data and drives a medical treatment of a patient by (1) assessing the patients' current physiological state and then (2) transitioning the physiology of the patient to a beneficial state by training the patient to auto-regulate their nervous system using a closed-loop VR biofeedback experience (i.e., VR Experience).

According to one embodiment, the VR System is used to treat a patient having a condition in need of treatment thereof. As referred to herein, the term "treatment of a patient", also referred to herein as "patient treatment", or "treat a patient", refers to the treatment of a patient having a medical condition, including ameliorating, reducing, managing or eliminating a medical condition in a patient, or improving the systematic functioning of a patient. Also included in the term "treatment of a patient" are physiological and psychological diseases or disorders. Examples of physiological disorders, include but are not limited to acute and chronic pain, diabetes, Alzheimer's disease and other dementia disorders, such as age-related dementia, high blood pressure, heart disease, sleep apnea, incontinence and irritable bowel syndrome (IBS). The VR System and method can also be used for the treatment of a patient having other medical conditions, typically classified as psychological or a combination of psychological/physiological, including but not limited to stress, anxiety, depression, post-traumatic stress disorder (PTSD), attention deficit hyperactivity disorder (ADHD), attention deficit disorder (ADD), obsessive compulsive disorder (OCD), insomnia, and phobias. The VR System and methods can also be used for the treatment of a patient to improve or optimize a patient's health, such as for meditation, training, sports performance, and other beneficial or rehabilitative therapies, such as for occupational therapy (e.g., to treat deficiencies in fine or gross motor skills), and speech therapy (e.g., to treat speech impediments).

The VR System and methods of the present invention provide a cost effective, non-invasive and non-pharmacological therapy for treatment of a patient. The VR Systems and methods as described herein are particularly useful in treating chronic disorders that require on-going monitoring and management for long-term amelioration, such as chronic pain.

In a preferred embodiment, the VR System and method are used for the treatment of chronic pain. The VR Biofeedback System analyzes and incorporates biometric data received from a patient to individualize, optimize, and control the VR System for chronic pain treatment in the patient.

Pharmacotherapy, physical therapy and psychological based therapies, such as CBT (cognitive behavioral therapy) are some of the main lines of treatment currently in use for pain management. However, many pain sufferers do not wish to use pharmacotherapy (due to side effects), and physical therapy, particularly where there is an underlying medical condition, is ineffective or can do further damage to the patient. There is limited availability of CBT or other psychological based therapies, and/or these type of therapies are of limited effectiveness and/or are cost prohibitive. The VR System according to the invention described herein, is non-invasive, and does not require pharmacotherapy. The VR System can be made widely accessible to the general public, either by at-home use, or use in a physical therapists (or physician, therapist, etc. or in a hospital) office, and is accordingly a cost effective treatment for a variety of medical conditions, particularly pain management.

Figure 1:
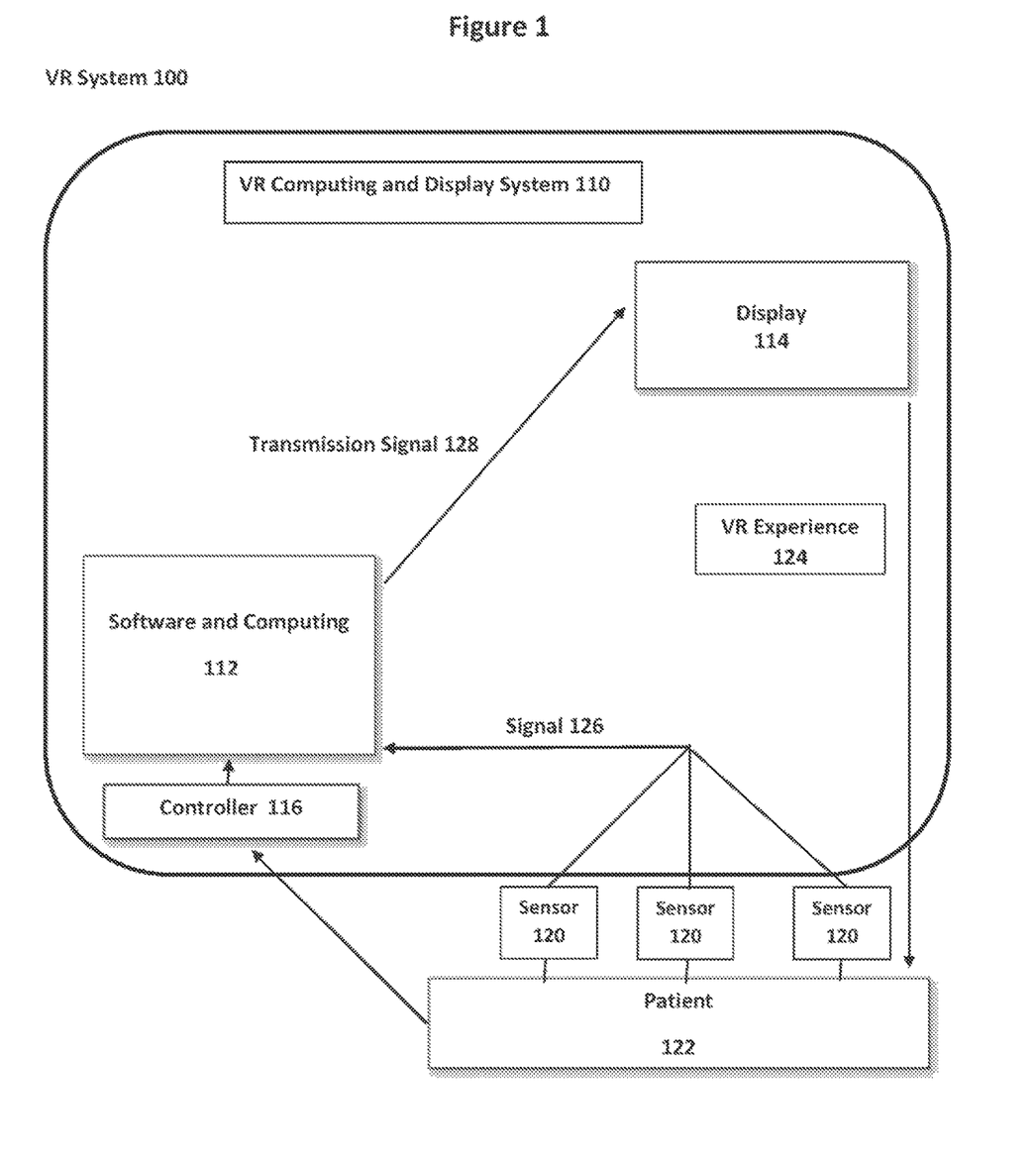
FIG. 1 is a schematic diagram showing the Virtual Reality System according to one embodiment of the invention.

Referring now to FIG. 1, the VR System 100 according the invention comprises a virtual reality computing and display system 110 which includes a virtual reality software system and computer system 112 having components for implementing and processing the virtual reality software system, and a controller 116 (optionally, the controller may be external). A display system 114 is in communication with the software and computer system 112, and the controller 116 is in communication with the VR software and computer system 112 and display system 114. The output of the virtual reality computing and display system is referred to herein as the VR Experience 124, which may include audio and visual, or physical output, as described herein. The VR System 100 can have one or more physiological sensors 120, for monitoring the physical response of the user (patient 122) to the VR Experience 124. The physiological sensors 120 are in communication with the VR software and computer system 112 and deliver the physiological signals 126 to the computing system 112, which alters the VR Experience 124 in response to the physiological signals 126. One or more sensors 120, such as biometric sensors, or other sensors that detect the physical response of the patient, are positioned on the patient's body (or remotely in some embodiments) and at least one physical signal 126 from the patient's body is monitored and transmitted to the VR computing and display system 110. In the VR Experience, the computing system 112 produces an output signal 128 which is delivered to the display system 114 to provide visual feedback to the subject's brain. The VR Experience 124 is adjusted according to the patient's ongoing physiological response to the VR Experience 124, while one or more of the patient's ongoing physical signals 120 are monitored and recorded. The VR Experience 124 adjusts in response to the physical signals 126 to treat the patient and/or improve the systematic functioning of the patient.

Figure 2:
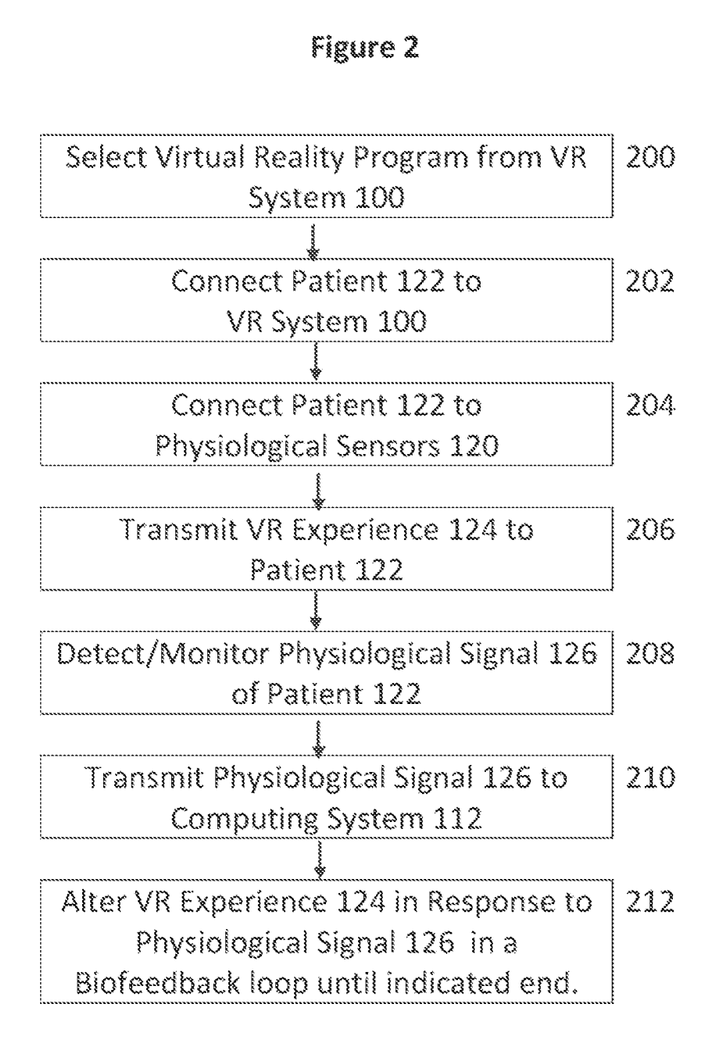
FIG. 2 is a flow chart showing the Virtual Reality System and Method according to another embodiment of the invention.

Referring now to FIG. 2, a flow chart showing the operation of the VR system and method is shown. First, in 200, a VR experience is selected from the VR system 100. Then, the patient 122 is connected to the VR system 100 via sensors 120 and visual and/or auditory and/or physical connection with the VR Display 114 (202, 204) Next, the VR Experience 124 is transmitted to the patient 122 (206) and one or more physical sensors 120 detect a signal from the patient 120 (208) and transmitted to the computing system 112 (210), The VR Experience 124 is varied in response to the physiological signal 126 in a biofeedback loop until and endpoint is reached (212).

The idea of the VR System and method is that, by harnessing the power of the mind in response to real-time physiological data, and becoming aware of what's going on inside the user's body, the user can gain more control over their health. When a user's body is under stress, either psychological stress, or physical stress, such as from pain, heart rate speeds up, muscles tighten, blood pressure rises, sweating occurs, and breathing quickens. Observing and controlling these physiological responses as they happen in the VR Experience, and then getting immediate feedback as the user attempts to control them, can improve a variety of medical conditions, particularly pain.

According to one embodiment of the invention, the system comprises one or more physiological sensors capable of sampling one or more of a user's physiological signals (also referred to herein as physiological data) and transmitting the user's physiological data to a processing device. Examples of physiological signals that can be captured include, but are not limited to pulse, heart rate, blood pressure, glucose levels, skin conductance, skin resistance, and brain waves, for example.

The system also provides a processing device capable of running virtual reality software (also referred to herein as VR Software). The processing device interfaces with peripheral system components.

The VR Software drives the user's VR Experience, processes the physiological data, and incorporates the physiological data into the VR Experience.

The term "VR Experience", as referred to herein refers to the user's experience when observing the output of the VR Software through a VR viewing device, such as a VR headset capable of delivering a stereoscopic images to the user, or other VR or augmented reality viewing devices and components, such as a 2D or 3D immersive screen, and other immersive gear designed to enhance the VR or augmented reality system, such as gloves or vests, designed to enhance feel in the VR System, and/or deliver sensory experience, such as vibration, motion trackers, VR equipped exercise and therapy equipment, such as bikes, balance boards, and pedals, for example, and immersive chairs, equipped with VR enhancements such as pedals and orientation tracking. As will be understood by those of skill in the art, the VR Experience is enhanced by the ability of the user to experience an atmosphere as closely replicating the natural world as possible. Detection and correction of movement can be integrated into treatment with the VR Experience in some embodiments. Accordingly, the VR Software and accompanying VR devices and immersive gear can be designed to detect tiny movements, vibrations, and directions. In some embodiments, the devices are specifically designed to monitor, measure and control these motions and directions through sensors, either applied directly to the user, or through external motion trackers.

A data storage system is also provided in the VR System according to the invention. The data storage system records physiological data and/or data from the VR Experience.

In some embodiments, an external server is connected to the system for optional communication across systems. The server provides an additional component of a social element to the VR Biofeedback System. According to this embodiment, two or more users can connect for communication, participation, and competition, either through data sharing (e.g., a social network), or a shared virtual reality.

The VR Biofeedback System comprises a closed-loop biofeedback system that both allows users to monitor their physiology, to guide the user to an optimal (or improved) physical state (as indicated by physiological monitoring) in the VR Experience. The optimized physical state achieved by the user in the VR Experience reduces the physiological effects of the user's medical condition. The physiological and user experience data acquired in the VR Experience can be stored in the system data storage, transmitted to the user and/or a third party (such as a doctor or physical therapist). The received physiological data can be used for real-time or post-experience analysis by the user or the third party.

The sensor system includes physiological sensors, and may include other VR sensors, such as gyroscopes, accelerometers, and other motion trackers, and voice and speech recognition and controls. The sensor system can include commercially available third-party sensors, or proprietary sensors developed by the inventors. The system includes one or more biometric sensors which are positioned on the patient's body and at least one physiological signal from the patient's body is monitored and transmitted to the VR computing and display system. The VR System can also have one or more physical sensors, for monitoring the physical response signal of the user to the VR Experience, either gross movements, or fine movements, such as eye contact. The physical sensors are in communication with the VR computing and display system and deliver the physical response signal to the computing system, which alters the VR Experience in response to the physical response signal. Speech recognition can be integrated into the system in some embodiments. The signals may be transmitted either wirelessly, through Bluetooth or Wi-Fi, or through a wired connection such as USB. The signals may be transmitted to the processing device along separate channels by each individual sensor, or may be packaged together by a microprocessor and transmitted along the same channel. The sensor system may also contain the data-storage system with a local hard-drive or memory stick and data-transmission directly from the microprocessor.

The processing device may include "VR-Ready" computers (computer with the necessary specifications to render VR to the target headset), mobile smartphones or tablets (such as an iPhone, iPad, Samsung Galaxy, or Google Pixel), or stand-alone Virtual Reality HMDs (such as the Oculus Go, Oculus Quest, Pico Goblin, Pico NEO, Lenovo Mirage Solo, HTC Vive Focus, etc.). The processing device may receive sensor data on any of the mentioned channels and through any of the mentioned protocols. The processing device may transmit stereoscopic images generated by the Virtual Reality Software to an external display via HDMI, USB, or Bluetooth, or may display the images through a built-in display. The processing device may also send data to the data-storage system or contain the data-storage system either in software or with a hardware storage device.

The headset device comprises VR headset devices such as:
- Tethered or untethered HMDs which are driven by a computer or game console and contain a stereoscopic display and optical delivery system (such as HTC Vive, Oculus Rift, or PSVR).
- Stand-alone HMDs that contain the processing device, stereoscopic display, and optical delivery system (such as the Oculus Go, Oculus Quest, Pico Goblin, Pico NEO, Lenovo Mirage Solo, HTC Vive Focus, etc.); and
- Passive headset which consists just of an optical delivery system to deliver stereoscopic images from a separate screen to the users' eyes (such as Samsung GearVR or Google Cardboard).

The data storage system comprises a storage device which may include a local, physical hard drive or memory card, a local, software directory on the processing device's operating system, or a remote server on a network. The data storage system may receive data directly from the sensor system, or may receive data from the Virtual Reality software. The data may be transmitted to the data storage device through software, through a wired or wireless network connection, and/or through embedded circuitry in the sensor system or processing device.

The virtual reality (VR) software operates on the processing device. The VR Software takes sensor data and any necessary control parameters (such as guiding parameter values, individualized user parameters, etc.) as an input, runs the virtual experience which is modulated in real-time by the physiological sensors, and outputs a stereoscopic rendering of the environment to a display in real-time. The software may contain multiple virtual experiences or just one. The software may also include capability to transmit or record data, as well as capability to connect to a server for embodiments of the invention that incorporate social experiences (e.g., connecting with other users on-line for a shared VR Experience, as described herein below).

The virtual reality (VR) experiences may be programmed in a game engine or captured through an optical system. They can include either or both of passive monitoring or guided modulation. Passive monitoring allows users to visualize their physiology in real-time without a guide. Guided modulation guides a users' physiology to an optimal state by modulating elements of the environment separate from the elements controlled by the user's physiological signals while the user controls elements with or visualizes their physiology in real-time. VR Experiences can be objective driven through gamification or through narrative, or they can be passive, without an objective. Each VR Experience may monitor or guide one or many physiological signals. Some experiences may have an optional social component or may be exclusively social. Social VR Experiences may allow users to communicate with each other directly through audio or video or indirectly through scores, leaderboards, messages, or physiological signals.

Social VR Experiences may be competitive, collaborative, or communicative. Competitive experiences allow users to compete against each other toward a certain objective. Collaborative experiences allow users to work together toward a certain objective. Communicative experiences allow users to interact and/or communicate unrelated to an objective. Collaborative and competitive experiences may be communicative as well.

Treatment for an individual may include one configuration of the prior mentioned system components or may include multiple, different configurations throughout the treatment process. The treatment process itself can last one session or can span multiple sessions across many months or years.

A typical session may be in the range of 15-30 minutes, but can be of any duration that is appropriate to the patient and the relevant condition subject to treatment. Throughout the treatment process, a user may select or be recommended (by medical expert or by automated software recommendation system) one or many different experiences. Sessions may be conducted in a clinic/hospital setting or may be conducted at home or elsewhere.

A typical session may be supervised or unsupervised. Supervised sessions are conducted by an operator who may assist in the application of sensors, modifying experience parameters, and collecting and recording data. Unsupervised sessions are conducted by the user, themselves. A session may consist of many stages, or may solely consist of the experience. Additional session stages may include but are not limited to profile generation, user customization, system calibration, baseline recording, and post experience recording, etc. The most important stage of the session is the experience, itself, which is the vehicle for delivering the intended medical benefits of the treatment. The experiences are pre-programmed and pm-designed, but may be customizable by the user to account for his/her individual preference and may be flexible to adjust (either through intelligent software or through user input) themselves to specified criteria or control parameters. An experience typically includes the following sections which may recur: customization, sensor calibration, instructions, physiological exercise (PHE), psychological exercise (PSE), and results. The various sections may overlap as well. There may be multiple physiological exercises (PHEs) depending on the experience and these exercises may be objective driven or passive and may be social or independent. The PHE is one of the core parts of the experience. It is in the PHE that users modulate or learn to modulate their physiology toward a desired goal (if objective driven) or by observation (if it is a passive exercise). The PHEs predominantly consist of biofeedback techniques and can either focus on one physiological signal or blend many. The idea behind PHEs is that if you show a user their physiological signals in real-time, they begin to learn how to control them consciously and/or subconsciously. Users can be guided to modulate their physiology to a desired state through visual or auditory stimuli.

Psychological Exercise (PSE) is another core part of the experience. PSE may implement various therapy techniques such as Cognitive Behavior Therapy (CBT), Acceptance and Commitment Therapy (ACT), Autogenic Training (AT). Visualization, Operant Behavior Therapy (OBT), etc. Where the PHEs focused on physical modulation of one's body, the PSE focuses on modulation of one's mind. There may be multiple PSEs in an experience and they may be customized for an individual based on their user profile, their input, or sensed data from the physiological sensors. Many PSEs involve embodiment in an avatar. Users may have the option to select a pre-created avatar, customize a pre-created avatar, or generate an avatar based on pictures or scans of their body. In one embodiment, a PSE is implemented into the VR Experience using one or more therapy techniques. This embodiment is particularly useful in the treatment of a psychological disorder which also has a physiological manifestation. In this embodiment, the VR Experience can involve a PSE using one or more therapy techniques, while the VR Experience simultaneously has the user regulate one or more physiological signals. In some embodiments, the VR Experience can train a patient to modulate the patient's physical response to known elements, also referred to herein as "stimuli" or "triggers", thus desensitizing the patient, and minimizing the patient's response to the stimuli or trigger. This combination therapy may be particularly useful in treatment of conditions such as anxiety, social anxiety, stress, PTSD, OCD, and phobias, where the patient has a psychological as well as physiological response to known elements. In another embodiment, the VR Experience incorporates Eye Movement Desensitization and Reprocessing (EMDR) therapy, where the VR Experience will have the patient recall distressing images or beliefs while receiving one of several types of bilateral sensory input, such as side-to-side eye movements or hand tapping. The PSE's described herein may be used alone, or in combination with a pharmacological treatment, and may be used alone or guided by a therapist.

EXAMPLES

Example 1

In an example of one embodiment according to the present invention, a biofeedback virtual reality system for pain reduction is described. Example 1 is a series of three exercises, the exercises being a combination of physiological exercises and psychological exercises, where the user (i.e., patient) is asked to perform a series of tasks that alter the virtual reality experience observed by the patient. The virtual reality computing and display system comprises an MSI Titan Laptop which is provided as the computer processing device, and incorporates the virtual reality software system, as described below. An Oculus Rift headset and tracking sensor are provided for the display system and receiving signal sensors (i.e., tracking sensors). The Oculus Rift headset and its tracking sensor are plugged into the MSI laptop via USB and HDMI for communication with the computing system.

A sensor system comprising a Muse EEG (brainwave sensor), Empatica E4 wristband (pulse and skin conductance sensor), and a proprietary respiration sensor are provided and positioned on the user's body. The Muse EEG is connected to the computer via Bluetooth and its data is sent to the VR Software by OSC messages generated by Muse's proprietary software. The Empatica E4 wristband transmits data to the VR Software directly via Bluetooth. The respiration sensor consists of a respiration transducer connected to a microprocessor which transmits data to the VR Software through USB.

The VR Software allows the user to sign into their profile. Once signed in, the user can select their desired VR Experience. The user selects Experience 1 (E1). Before E1 begins it checks to make sure all of the necessary sensors are connected for this specific experience. If a sensor is not connected, it prompts the user to connect it. E1 begins by allowing the user to select and customize an avatar or select an avatar already saved in their profile. With the avatar selected and customized, the experience moves into a brain wave exercise.

For Example 1, the user Experience (E1), described below is a brain wave exercise. The brain wave exercise works as follows: First, the user is situated in a relaxing alpine or other preferably natural VR environment. A boulder floats in front of the user, the boulder incorporating a faded outline of a larger version of the boulder. The boulder's size is controlled by the relative average amount of the user's alpha waves. When the alpha level grows, the boulder grows. When the alpha level shrinks, so does the boulder. The user's goal is to keep the boulder larger than the faded outline. The time the boulder spends being larger than the outline is added to the user's score. The user tries to score as high as possible for a set time limit, either set by the user, or set automatically by the software, for example, 5 minutes. In addition to the visual feedback provided by the size of the boulder, there is a tone which changes pitch in correspondence with the user's alpha level. This auditory feedback can be toggled on or off by the user. As described in Experiment 1, the sensors continuously monitor the patient's brainwaves, pulse, skin conductance, and respiration. The VR Experience is continuously altered in the form of the boulder size, either growing or shrinking in response to the patient's brainwaves. Accordingly, the user engages in closed loop biofeedback VR Experience to increase the user's alpha brain waves.

After the set time limit, the VR Software can transition the user to a second exercise, described in this Example as a respiration exercise. During the respiration exercise instructions, the user is prompted to take a deep breath. This allows the sensor to calibrate itself. The respiration exercise works as follows: the user remains situated in the relaxing alpine environment (or other environment) but the scene transitions to a night or otherwise dark scene. The user is asked to create a fire. There is a campfire in front of the user that is controlled by the user's breathing. Next to the fire, there are bellows pumping air into the fire. The user is told to match their breathing to the bellows. Inhaling when the bellows extends, exhaling when the bellows compresses. The closer the user's breathing matches the bellows, the larger the fire grows. The breathing exercise can be set at different intervals and time limits, depending on the needs of the user, and the user's particular medical condition. For example, the bellows can begin at 10 breaths per minute, hut in 5 minutes slow to 6 breaths per minute. The exercise can stay at 6 breaths per minute for another 5 minutes, or transition to another breathing interval. The time the user spends with their breathing following the bellows with accuracy above a certain level is added to the user's score. Their goal is to maximize their score in the allotted time (e.g., a 10 minute breathing period). Accordingly, the user engages in closed loop biofeedback to improve the user's respiratory function and/or other functions associated with controlled deep breathing, such as improved heart rate, heart rate variability, heart rate coherence, and pulse.

After the breathing exercise is over, the scene can transition to another environment, in this example, the environment is a crystal cave. The crystals are reflective and the user sees themselves (their avatar) in the reflection. When the user moves their head and torso in real life, the avatar mimics the user's real life experience. After the user looks at themselves for a time period, for example, 15 seconds, the avatar body can fade away to reveal a second avatar of the user's skeleton with burning flames, or another suitable bodily representation in the avatar of where the pain in the user's physical body resides. After a time period, such as 5 seconds, the image (e.g., flames) fade to another soothing color, such as blue and then float away from the user's avatar body. After this visualization exercise, the scores are displayed and the user may compare their scores to a public leaderboard or exit the experience. Accordingly, the user engages in a psychological exercise to improve the user's pain management and/or improve other physiological functions associated with pain management, such as decreased heart rate and pulse.

Throughout the experience, the VR Software receives physiological data, such as EEG, pulse, skin conductance, and respiration data and preferably conveys them to a server or local data storage. Experience data is also sent with the physiological data, such as what exercises the user performed, and the user's performance (e.g., score earned in the experience). This data can later be analyzed by the VR Software's data analytics tools or can be accessed by a third party, such as the user's doctor.

Example 2

In another example of an embodiment according to the present invention, a biofeedback virtual reality system for pain reduction is described. Example 2 is a series of two exercises, the exercises, where the user (i.e., patient) is asked to perform a series of tasks that alter the virtual reality experience observed by the patient. The two exercises in Example 2 also incorporate a social experience into the VR Experience. The virtual reality computing and display system comprises a Samsung Galaxy S8 processing and display device and a Samsung Gear VR headset. The sensor system comprises a Heart Math heart rate sensor and a Vernier GDX-RB Respiration Belt.

The Heart Math sensor is paired with the Samsung Galaxy S8 and transmits its data into the VR Software through Bluetooth. The respiration sensor connects to and transmits data to the Samsung Galaxy S8 via Bluetooth as well. The Samsung Galaxy S8 is placed into the Samsung Gear VR headset which allows stereoscopic display. The VR Software comprises an android app.

The VR Software allows the user to sign into their profile. Once signed in, the user can select their desired VR Experience. The user selects Experience 2 (E2). E2 is a multiplayer experience. Before E2 begins, the system checks to make sure all of the necessary sensors are connected for this specific experience. If a sensor is not connected, it prompts the user to connect it. E2 begins by allowing the user to select and customize an avatar or select an avatar already saved in their profile. With the avatar selected, the experiences moves into a waiting room while the system connects to the server to find an opponent. Once an opponent is found and a network connection is established between the two users, the experience transitions to a breathing exercise.

The breathing exercise operates as follows: The user is located atop clouds in the sky. All around the user, in the distance, the user can see a sinusoidal track made of clouds with clouds distinguishing the top and bottom of the track. Inside the track there are Pegasuses (or other flying animals or mythical creatures). When the user inhales, the user's Pegasus moves up and when the user exhales the Pegasus moves down. There is a Pegasus for each user. The user is instructed to keep the Pegasus flying in the track. If the Pegasus touches the top or the bottom of the track, the Pegasus moves backward slightly. If the Pegasus flies perfectly without hitting any obstacles for 20 seconds the Pegasus moves forward along the track. The track starts rotating around the users and they must inhale and exhale to keep the Pegasus inside the track as it undulates due to its sinusoidal shape. The track moves at a speed that encourages the users to breath at 6 breaths per minute. After 10 minutes the exercise ends and the user whose Pegasus is in front is the winner. The experience then transitions to a heart rate variability experience.

In the heart rate variability experience, the users are still in the clouds but now they are controlling dragons. The dragons are rigged with nodes along their lengths and the height of each node is controlled by the user's heart rate (HR) or previous heart rates. The nodes are controlled by a buffer of previous heart rate values such that the head's height is determined by the current value, the node behind the head corresponds to the previous HR value, the node behind corresponds to HR value before the previous value, and so on. The buffer contains 10 values and so the dragon has 10 nodes. The buffer may be represented as [HR(t-9), HR(t-8), HR(t-7), HR(t-6), HR(t-5), HR(t-4), HR(t-3), HR(t-2), HR(t-1), HR(t)], where HR(t) is the heart rate at the current timestep and HR(t-n) is the heart rate of the $n^{th}$ previous timestep. Each time the user's heart beats, the values are shifted to the left, the leftmost value is discarded, and the rightmost value is the new HR value. For example: if the buffer of previous HR values was [60,61,62,62,63,63,62,61,60,59] and the new value is 58, the new buffer is [61,62,62,63,63,62,61,60,59,58]. The goal of this exercise is to increase and control one's heart rate variability. Without control of (heart rate variability) the dragon will move randomly and minimally, but with control of HRV the dragon can be controlled to move in a sinusoidal fashion. With optimal heart rate variance and coherence, the HR will increase as the user inhales and decrease as the user exhales, leading their dragon to assume the mentioned sinusoidal position, following the user's breath. The users see each other's dragons and the user who can keep their dragon moving most sinusoidally for the longest amount of time wins.

After the HRV exercise is over, the user's scores are displayed and the users are given the chance to rematch and replay the experiences.

Throughout the experience, the VR Software is sending pulse, and respiration data to a server and from the server to the other user's device. The server records the data in addition to forwarding it to the other user (or a third party as designated by the user). Experience data is also sent with the physiological data, such as what exercise they were in and their score at that moment. This data can later be analyzed by the VR Software's data analytics tools or can be accessed by a third party, such as the user's doctor.

The invention claimed is:

1. A method of treating a patient using a virtual reality biofeedback experience, the method comprising:
  providing the patient with a first virtual reality computing and display system operative to present a shared virtual reality experience that depicts a first virtual object in a first state, wherein the first virtual object does not represent the patient and does not represent a symptom the patient is experiencing;
  providing another patient with a second virtual reality computing and display system operative to present the shared virtual reality experience that depicts a second virtual object in the first state, wherein the second virtual object does not represent the patient and does not represent a symptom the patient is experiencing;
  receiving physiological data that represents modulation of the mind or body of the patient and the another patient while the shared virtual reality experience is provided to the patient;
  altering the shared virtual reality experience by causing the first virtual object to transition from the first state to a second state in response to processing the received physiological data of the patient while patient is trained to auto-regulate his or her nervous system to maintain the first virtual object in the second state as a function of additional physiological data;

altering the shared virtual reality experience by causing the second virtual object to transition from the first state to a second state in response to processing the received physiological data of the another patient while the another patient is trained to auto-regulate his or her nervous system to maintain the second virtual object in the second state as a function of additional physiological data; and determining which of the patient and the another patient maintains the respective first virtual object and second virtual object in the second state for an amount of time.

2. The method of claim 1 comprising:

positioning one or more physiological sensors on a body of the patient, a given sensor capable of monitoring at least one physiological signal from the body of the patient to produce and transmit physiological data.

3. The method of claim 1 comprising:

positioning one or more physiological sensors on a body of the another patient, a given sensor capable of monitoring at least one physiological signal from the body of the patient to produce and transmit physiological data.

4. The method of claim 1 comprising awarding one or more points based on an outcome of the determination.

5. The method of claim 4 comprising wherein awarding comprises entering a win state when one of the patient or the another patient accumulates sufficient points.

6. The method of claim 5 wherein entering a win state comprises resetting the shared virtual reality experience for a rematch between the patient and the another patient.

7. The method of claim 5 wherein entering a win state comprises displaying a first score for the first patient and a second score for the another patient on a leader board, the first score and the second score are based upon the one or more awarded points.

8. The method of claim 1 wherein providing the patient with a first virtual reality computing and display system operative to present the shared virtual reality experience that depicts the first virtual object in a first state comprises moving the first virtual object along a random path.

9. The method of claim 1 wherein altering by causing the first virtual object to transition from the first state to the second state comprises moving the first virtual object along a predetermined path.

10. The method of claim 9 wherein moving the first virtual object in the predetermined path comprises moving along a sinusoidal path.

11. The method of claim 1 wherein providing the another patient with the second virtual reality computing and display system operative to present the shared virtual reality experience that depicts the second virtual object in the first state comprises moving the second virtual object along a random path.

12. The method of claim 11 wherein altering by causing the second virtual object to transition from the first state to the second state comprises moving the first virtual object along a predetermined path.

13. The method of claim 11 wherein moving the second virtual object in the predetermined path comprises moving along a sinusoidal path.

14. The method of claim 1 comprising storing the received physiological data.

15. The method of claim 14 wherein storing further comprises transmitting the received physiological data to a third party.

16. The method of claim 14 wherein transmitting comprises transmitting to a set of physicians selected from the set consisting of a doctor and a physical therapist.

17. A method of treating a patient using a virtual reality biofeedback experience in a virtual reality computing and display system, the method comprising:

providing, by the virtual reality computing and display system, a virtual reality experience to a patient, the virtual reality experience having one or more conditions that can be altered by the patient;

monitoring, by the virtual reality computing and display system, at least one physiological signal from the patient body to produce physiological data;

presenting, by the virtual reality computing and display system, a virtual object in a first state, wherein the virtual object does not represent the patient and does not represent a symptom the patient is experiencing;

receiving, by the virtual reality computing and display system, physiological data that represents modulation of the mind or body of the patient while the virtual reality experience is provided to the patient; and processing, by the virtual reality computing and display system, the received physiological data to alter the virtual reality experience by causing the virtual object to transition from the first state to a second state while the patient is trained to auto-regulate his or her nervous system to maintain the virtual object in the second state in the virtual reality experience as a function of additional physiological data received by the virtual reality computing and display system.

* * * * *

UNITED STATES PATENT AND TRADEMARK OFFICE
CERTIFICATE OF CORRECTION

| | | |
|---|---|---|
| PATENT NO. | : 11,490,857 B2 | Page 1 of 1 |
| APPLICATION NO. | : 17/357028 | |
| DATED | : November 8, 2022 | |
| INVENTOR(S) | : Celine Tien, Julien Soros and Narae Kim | |

It is certified that error appears in the above-identified patent and that said Letters Patent is hereby corrected as shown below:

On the Title Page

Item (60) "Provisional application No. 61/613,377, filed on Mar. 20, 2012." should be --Provisional application No. 62/613,377, filed on Jan. 3, 2018.--

Signed and Sealed this
Twenty-first Day of February, 2023

*Katherine Kelly Vidal*

Katherine Kelly Vidal
*Director of the United States Patent and Trademark Office*